United States Patent
Oftring et al.

(10) Patent No.: US 7,754,911 B2
(45) Date of Patent: Jul. 13, 2010

(54) METHOD FOR ISOLATING METHYL GLYCINE NITRILE-N,N-DIACETONITRILES FROM AN AQUEOUS CRUDE MIXTURE

(75) Inventors: Alfred Oftring, Bad Duerkheim (DE); Bernd Judat, Mannheim (DE); Matthias Rauls, Ludwigshafen (DE); Katrin Friese, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 223 days.

(21) Appl. No.: 11/913,726

(22) PCT Filed: May 3, 2006

(86) PCT No.: PCT/EP2006/062008
§ 371 (c)(1),
(2), (4) Date: Nov. 6, 2007

(87) PCT Pub. No.: WO2006/120144
PCT Pub. Date: Nov. 16, 2006

(65) Prior Publication Data
US 2008/0194858 A1 Aug. 14, 2008

(30) Foreign Application Priority Data
May 6, 2005 (DE) .................. 10 2005 021 056

(51) Int. Cl.
*C07C 255/00* (2006.01)
(52) U.S. Cl. .................................................. 558/452
(58) Field of Classification Search ................ 558/452
See application file for complete search history.

(56) References Cited

U.S. PATENT DOCUMENTS

| 5,786,313 A | 7/1998 | Schneider et al. |
| 5,849,950 A | 12/1998 | Greindl et al. |
| 2003/0166968 A1 | 9/2003 | Schulz et al. |

FOREIGN PATENT DOCUMENTS

| DE | 32 46 494 A1 | 6/1984 |
| WO | WO 94/29421 | 12/1994 |
| WO | WO 01/90041 A1 | 11/2001 |

OTHER PUBLICATIONS

A. M. Hilton, et al. "Emulsion solidification of meta-chloronitrobenzene: purification and crystallisation", Journal of Crystal Growth, XP 004053484, vol. 166, Sep. 1996, pp. 971-975.

*Primary Examiner*—Rei-tsang Shiao
(74) *Attorney, Agent, or Firm*—Oblon, Spivak, McClelland, Maier & Neustadt, L.L.P.

(57) ABSTRACT

The invention relates to a process for isolating methylglycinenitrile-N,N-diacetonitrile (MGDN) from an aqueous emulsion which comprises MGDN and has an MGDN content of 3-50% by weight in a crystallizer, comprising the steps:
(a) the aqueous emulsion is, starting from a temperature above the solidification point, cooled to a temperature below the solidification point, the cooling rate averaged over time not exceeding 5 K/h, until substantially the entirety of the emulsified MGDN has solidified,
(b) the resulting aqueous suspension is cooled further and/or concentrated, and the cooling rate may be greater than in step (a).

7 Claims, 3 Drawing Sheets

METHOD FOR ISOLATING METHYL GLYCINE NITRILE-N,N-DIACETONITRILES FROM AN AQUEOUS CRUDE MIXTURE

The invention relates to a process for isolating methylglycinenitrile-N,N-diacetonitrile from an aqueous crude mixture, as is obtained in the preparation of methylglycinenitrile-N,N-diacetonitrile.

The aminopolyphosphonates, polycarboxylates or aminopolycarboxylates, such as ethylenediaminetetraacetic acid (EDTA), which are frequently used as complexing agents in domestic detergents are biodegradable only to a certain degree. An inexpensive alternative is provided by the glycine-N,N-diacetic acid derivatives, such as methylglycine-N,N-diacetic acid (MGDA), which is nontoxic and readily biodegradable. The use of MGDA and of related glycine-N,N-diacetic acid derivatives in detergents and their syntheses are described in WO-A 94/29421 and U.S. Pat. No. 5,849,950. For inexpensive production of the glycine-N,N-diacetic acid derivatives, high demands are made on the yield of the individual synthesis steps and purity of the isolated intermediates.

MGDA is prepared by reacting iminodiacetonitrile with acetaldehyde and hydrocyanic acid or of alpha-alaninenitrile with formaldehyde and hydrocyanic acid, and alkaline hydrolysis of the MGDN obtained as an intermediate with sodium hydroxide solution to obtain the trisodium salt of MGDA. In order to achieve high MGDA yields, it is desirable to isolate MGDN as an intermediate and to use it as a pure substance in the hydrolysis step which follows. In U.S. Pat. No. 5,849,950, example 2, MGDN is crystallized out of the crude product mixture of the reaction of ACN, formaldehyde and alaninenitrile which is obtained in a preceding step in situ from acetaldehyde, HCN and ammonia, by cooling the product mixture.

The aqueous crude mixture comprising MGDN can comprise a series of secondary components. When MGDN is prepared by pH-controlled Strecker reaction of iminodiacetonitrile (IDN) with acetaldehyde and hydrocyanic acid, IDN can either be used as a crystalline raw material or else be obtained by pH-controlled reaction of urotropin with HCN in aqueous solution and be converted to MGDN without isolation. As secondary components, the aqueous MGDN crude mixture then comprises ammonium sulfate, acetaldehyde cyanohydrin, formaldehyde cyanohydrin, methylenebisiminodiacetonitrile (MBIDN), nitrilotriacetonitrile (NTN), and unconverted reactants.

MGDN has highly temperature-dependent solubility in water. For instance, only about 0.5% by weight of MGDN dissolves at 10° C. in water or an aqueous ammonium sulfate solution. At approx. 60° C., the solubility is still about 5% by weight. Above approx. 60° C., an emulsion of MGDN and its aqueous solution with more than 5% by weight of dissolved MGDN is present. No phase diagram of the water-MGDN system is known.

Owing to the high temperature dependence of the solubility of MGDN in water, MGDN can be isolated from its aqueous solution by cooling crystallization and subsequent solid/liquid separation. In the course of cooling of an aqueous solution or emulsion of MGDN, MGDN precipitates out as a solid in the form of fine, needle-like crystals which agglomerate. The mother liquor incorporated in the agglomerates comprises, as impurities, all secondary components of the MGDN synthesis, so that the moist crystals removed by filtration have a dark brown color. In the cooling crystallization, encrustations additionally occur on the walls of the crystallizer.

It is an object of the invention to provide an improved process for removing MGDN from the aqueous crude product mixtures obtained in its preparation.

The object is achieved by a process for isolating methylglycinenitrile-N,N-diacetonitrile (MGDN) from an aqueous emulsion which comprises MGDN and has an MGDN content of 3-50% by weight in a crystallizer, comprising the steps:
(a) the aqueous emulsion is, starting from a temperature above the solidification point, cooled to a temperature below the solidification point, the cooling rate averaged over time not exceeding 5 K/h, until substantially the entirety of the emulsified MGDN has solidified,
(b) the resulting aqueous suspension is cooled further and/or concentrated, and the cooling rate may be greater than in step (a).

Figure 1:
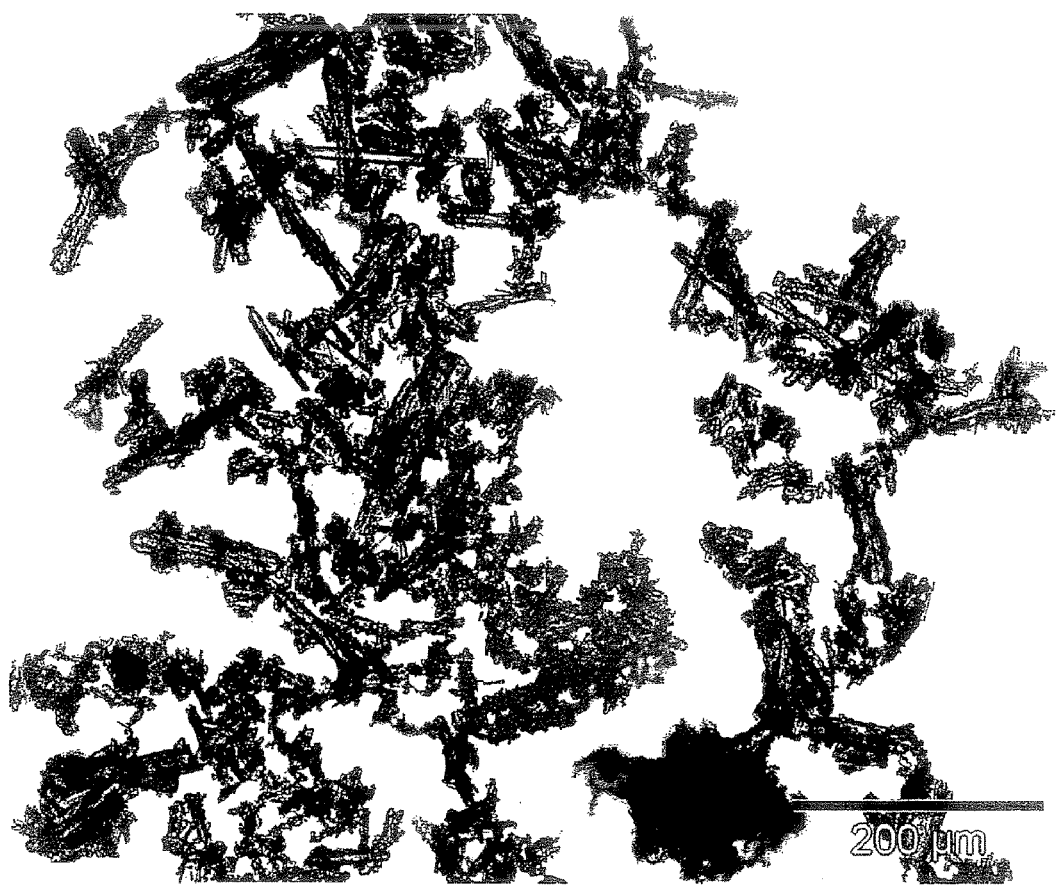
FIG. 1 is a microscopic view of MGDN crystals isolated by a comparative process.

It is essential that the crude product mixture which comprises MGDN and is present above the solidification point of MGDN as an emulsion of MGDN as a disperse organic phase in a saturated aqueous MGDN solution as a continuous aqueous phase is cooled below the solidification point in step (a), averaged over time, only very slowly, i.e. with a low cooling rate (expressed in K/h). The solidification point is that temperature at which MGDN of the given purity solidifies, i.e. the MGDN droplets emulsified in the aqueous phase solidify. This point may, depending on the type and amount of the impurities present in the MGDN, vary by a few ° C. and is approx 65° C. for pure MGDN.

The cooling rate in step (a), averaged over time, is ≦5 K/h, preferably ≦3 K/h. The cooling rate may in principle be as small as desired; for practical purposes, it is generally from 1 K/h to 5 K/h. The instantaneous cooling rate may be constant or vary provided that, up to the ti me at which virtually the entirety of the emulsified MGDN has been converted from the liquid into the solid (crystalline) state, i.e. a suspension has formed from the emulsion, the cooling rate averaged over time does not exceed the specified limiting value. For example, the emulsion can first be cooled rapidly, at a rate which momentarily significantly exceeds the specified limiting value, and subsequently cooled further with a much lower cooling rate which is distinctly below the specified limiting value, or the temperature is subsequently kept substantially constant for a period, until virtually all of the emulsified MGDN has solidified. For example, the emulsion can be cooled "rapidly", for example with an instantaneous cooling rate of >5 K/h, to a temperature up to 10° C. below the solidification point, which is followed by a "hold time" during which the temperature is kept substantially constant until virtually all of the emulsified MGDN has solidified. For example, this hold time may be from 0.5 to 2 h.

The aqueous emulsion can be cooled in step (a) by allowing water to evaporate and/or by removing heat via the crystallizer wall.

In the step (b) which follows, the resulting aqueous suspension can be cooled further and/or concentrated, and the cooling rate can be greater than in step (a).

The slow cooling of the suspension in step (a) ensures that the emulsified MGDN has already solidified and is present in crystalline form before there is significant crystallization of dissolved MGDN out of solution as a result of further cooling of the MGDN/water mixture. Thus, the solidification of the emulsified MGDN and the crystallization of dissolved MGDN out of solution are separated in time. This substantially suppresses new formation of crystal seeds, as a result of which the formation of fines is prevented. The MGDN then crystallizes out of solution quite predominantly on the already present coarse MGDN crystals. This effect does not occur when excessively rapid cooling results in essentially simultaneous solidification of the emulsified MGDN droplets and crystallization of dissolved MGDN.

During the crystallization operation, preference is given to evaporating water out of the aqueous mixture for at least some time, in which case this evaporation operation may be accompanied by cooling and/or concentration of the mixture. As a result of the evaporation, a zone of supersaturation forms, essentially adjoining the liquid/gas space interface of the aqueous mixture, in which there is an increased crystallization of MGDN out of solution. When further crystal seeds are formed, they are formed only in the relatively narrow zone of supersaturation in the vicinity of the interface, so that their number is restricted. These are subsequently transported into the interior of the suspension, where they grow further at only low supersaturation.

Preference is to be given to cooling by allowing water to evaporate over cooling by removing heat via the vessel wall, provided that evaporative cooling is still technically possible without any problem. This also prevents MGDN crystals from being deposited on the crystallizer wall, and there being encrustation of the crystallizer wall. It is generally possible without any problem for there to be evaporative cooling down to a temperature of the aqueous mixture of approx. 30° C.

The mixture may be cooled and the water fraction of the mixture kept substantially constant. The mixture is cooled by the withdrawal of heat by the evaporation operation when the evaporation operation is carried out substantially (or at least partially) adiabatically. The water content of the MGDN mixture is kept substantially constant by virtue of the water vapor condensing and running back into the mixture (working with "total reflux"). The evaporation is brought about by pressure reduction to a pressure below the partial pressure of water vapor in the mixture at the particular temperature.

Alternatively, the mixture can be concentrated by evaporating water, in which case the temperature is kept substantially constant, i.e. the evaporation operation is carried out substantially isothermally.

The mixture may either be cooled or concentrated by evaporating water. These two operations may be carried out simultaneously or successively. Both operations take place successively when the evaporation operation is carried adiabatically and the evaporated water is not fully replaced, i.e. for example, there is only partial reflux of the condensed water or no reflux. However, it is also possible for example first to carry out an isothermal evaporation with an increase in concentration and then an adiabatic evaporation, in which case it is possible to work with total, partial reflux or without reflux.

In one embodiment of the process according to the invention, cooling is effected in step (b) by evaporative cooling, in which case it is carried out until the temperature of the mixture has fallen at least to 30° C. It is further preferred to remove heat via the crystallizer wall as soon as the temperature goes below approx. 30° C. or lower. It is further preferred to maintain a cooling rate in step (b) which, averaged over time, is at least 5 K/h, preferably $\geq$7.5 K/h, in particular in the range from 10 to 30 K/h.

Preference is given to cooling in step (b) to a temperature below 20° C. This achieves substantial crystallization of the dissolved MGDN.

According to the invention, larger crystals are formed overall. However, less mother liquor adheres to them; in particular, no mother liquor can be "incorporated" into agglomerates of ultrafine crystals, or the adhering mother liquor can be removed readily, for example by simple filtering or centrifugation. This considerably reduces the complexity of purification. Encrustation of the walls of the crystallizer is also effectively prevented.

The MGDN concentration of the aqueous crude product mixture is generally from 3 to 50% by weight, preferably from 15 to 40% by weight, more preferably from 20 to 35% by weight. A content of dissolved MGDN of 1% by weight corresponds to a crystallization temperature of approx. 20° C., a content of dissolved MCDN of 5% by weight to a crystallization temperature of approx. 55° C. At 10° C., the water solubility of MGDN is still about 0.5% by weight.

At only low MGDN contents of the mixture of generally up to 10% by weight, it may be appropriate at the start of the crystallization operation to carry out a so-called "seeding loop", i.e. first to reheat the mixture by a few ° C. after crystal formation in order to redissolve a portion of the crystals formed, and subsequently to cool it again.

In one embodiment of the process according to the invention, the aqueous mixture is cooled in step (b) by evaporating water, in the course of which the MGDN concentration of the mixture is kept substantially constant. This variant can also be referred to as "vacuum cooling crystallization" which is carried out with total reflux.

In a further embodiment of the process according to the invention, the aqueous mixture is concentrated in step (b) by evaporating water, in the course of which the temperature of the mixture is kept substantially constant. This variant can also be referred to as "isothermal evaporative crystallization".

In a further embodiment of the process according to the invention, step (b) comprises both cooling and concentration of the aqueous mixture, these two operations proceeding simultaneously or successively. In a preferred variant of this embodiment, a vacuum cooling crystallization is carried out with only partial reflux of the condensed water vapor or without reflux.

The design of the crystallizer in which the process according to the invention is carried out may be any desired design. It may, for example, be a stirred tank crystallizer, force circulation crystallizer, guide tube crystallizer or fluidized bed crystallizer, for example of the Oslo type. The process according to the invention may be carried out batchwise, semicontinuously or continuously. It is preferably carried out batchwise, for example in a stirred tank crystallizer.

The crystals can be removed by solid/liquid separation with any solid/liquid separation apparatus, for example a suction filter, a rotary filter, a belt filter, a pusher centrifuge, a bowl centrifuge or the like. The removed crystals may subsequently be washed, for example with water or the starting mixture of the crystallization as a wash liquid.

The aqueous crude product mixture comprising MGDN from which MGDN is isolated by the process according to the invention is generally obtained by 1. Reacting iminodiacetonitrile (IDN) with HCN and acetaldehyde in aqueous solution, iminodiacetonitrile can be obtained as an aqueous emulsion in a preceding stage from urotropin and hydrocyanic acid or from formaldehyde cyanohydrin and ammonia.
2. Reacting alaninenitrile with HCN and formaldehyde in aqueous solution. Alaninenitrile may be obtained in a preceding stage from acetaldehyde, HCN and ammonia or acetaldehyde cyanohydrin and ammonia.

Preference is given to obtaining an aqueous crude product mixture comprising MGDN as follows:

1a. Iminodiacetonitrile (IDN) is converted by reacting urotropin, which can be obtained in situ from ammonia and formaldehyde, with hydrocyanic acid at a pH of from 5.5 to 6.3, preferably from 5.7 to 6.1, more preferably from 5.8 to 6.0, and a temperature in the range from 20 to 90° C., preferably from 25 to 80° C. The molar ammonia:formaldehyde:hydrocyanic acid ratio is generally 1:1.5:1.5-1.9; the IDN concentration in the resulting aqueous emulsion is generally 15-40% by weight, preferably 20-35% by weight. Subsequently, the pH of the aqueous IDN emulsion is adjusted with mineral acid to 2-1.0, preferably 1.8-1.5, more preferably 1.8-1.7. The acidified IDN emulsion is then reacted with acetaldehyde and hydrocyanic acid to give MGDN. The molar IDN:acetaldehyde:HCN ratio is generally 1:1-1.2:1-1.2, preferably 1:1.0-1.1:1.1-1.2; the temperature in the reaction is generally 40-90° C., preferably 50-80° C. The MGDN concentration of the resulting aqueous emulsion is generally 20-50% by weight, preferably 25-40% by weight. Before the crystallization is carried out, preference is given to diluting the aqueous emulsion with water to an MGDN content of 15-40% by weight, preferably 20-35% by weight.

IDN can also be prepared by reacting formaldehyde cyanohydrin with ammonia. Alternatively, the starting material used as the reactant may be crystalline IDN which is emulsified in water.

2a. Alpha-alaninenitrile (AN) is prepared by reacting excess ammonia with acetaldehyde and HCN or by reacting acetaldehyde cyanohydrin with excess ammonia, ammonia being used as an aqueous solution, in gaseous form or in liquid form. The reaction may be carried out under pressure. The excess ammonia is preferably distilled off under reduced pressure. The crude AN is reacted with formaldehyde and hydrocyanic acid to give MGDN. To this end, the pH of the aqueous AN solution is adjusted with mineral acid to 2-1.0, preferably to 1.8-1.5, more preferably to 1.8-1.7. The molar AN:formaldehyde:HCN ratio is generally 1:1.0-1.2:1.0-1.2; the temperature in the reaction is generally 40-90° C., preferably 50-80° C. The MGDN concentration of the resulting aqueous emulsion is generally 20-50% by weight, preferably 25-40% by weight. Before the crystallization is carried out, the aqueous emulsion is preferably diluted with water to an MGDN content of 15-40% by weight, preferably 20-35% by weight.

The invention is illustrated in detail by the examples which follow.

EXAMPLES

Preparation of an Aqueous MGDN Crude Emulsion

Example 1

IDN is prepared by reacting a solution of 173.9 g (1.241 mol) of urotropin in 535 g of water with 210.9 g (7.814 mol) of hydrocyanic acid. To regulate the pH to 5.8-5.9, a total of 188 g of 50% by weight sulfuric acid are metered in. This results in 1090 g of an aqueous solution which comprises 336.3 g (3.54 mol) of IDN (95% yield based on formaldehyde). The pH of the solution is adjusted to 1.8 and its temperature to 60° C. by adding 60 g (0.306 mol) of 50% by weight sulfuric acid. Subsequently, 105.1 g (3.894 mol) of HCN and 171.6 g (3.894 mol) of acetaldehyde are metered in within 75 min. The temperature rises to approx. 80° C. The mixture is stirred at 80° C. for a further 60 minutes. During the addition of the reactants and during the postreaction, the pH falls to approx. 1.2. This results in approx. 1440 g of an approx. 36% by weight MGDN emulsion which comprises 515 g of MGDN (3.469 mol; 98% yield based on IDN).

Isolation of MGDN from the Crude Emulsion

Comparative Example

A 1 l jacketed stirred vessel made of glass as a crystallizer is initially charged with 1120 g of an 8% by weight aqueous MGDN emulsion at 70° C. with stirring. The temperature-control fluid in the jacket is used to cool the solution to 61° C. This forms a very large number of crystal seeds. After the heating to 64° C. just below the solidification point, a portion of these seeds disappears again. Subsequently, the mixture is cooled down to 10° C. by brine cooling at a cooling rate of 10 K/h with stirring. The precipitated crystals are removed with a suction filter. As can be seen under the microscope (FIG. 1), the crystals comprise, in addition to approx. 100 µm-long needle-like crystals, predominantly fines of size <10 µm. Since the crystals tend to agglomerate and mother liquor adheres between the crystals, the moist crystals take on the intense brown color of the mother liquor. The container walls of the crystallizer have severe encrustations.

Example 2

Figure 2:
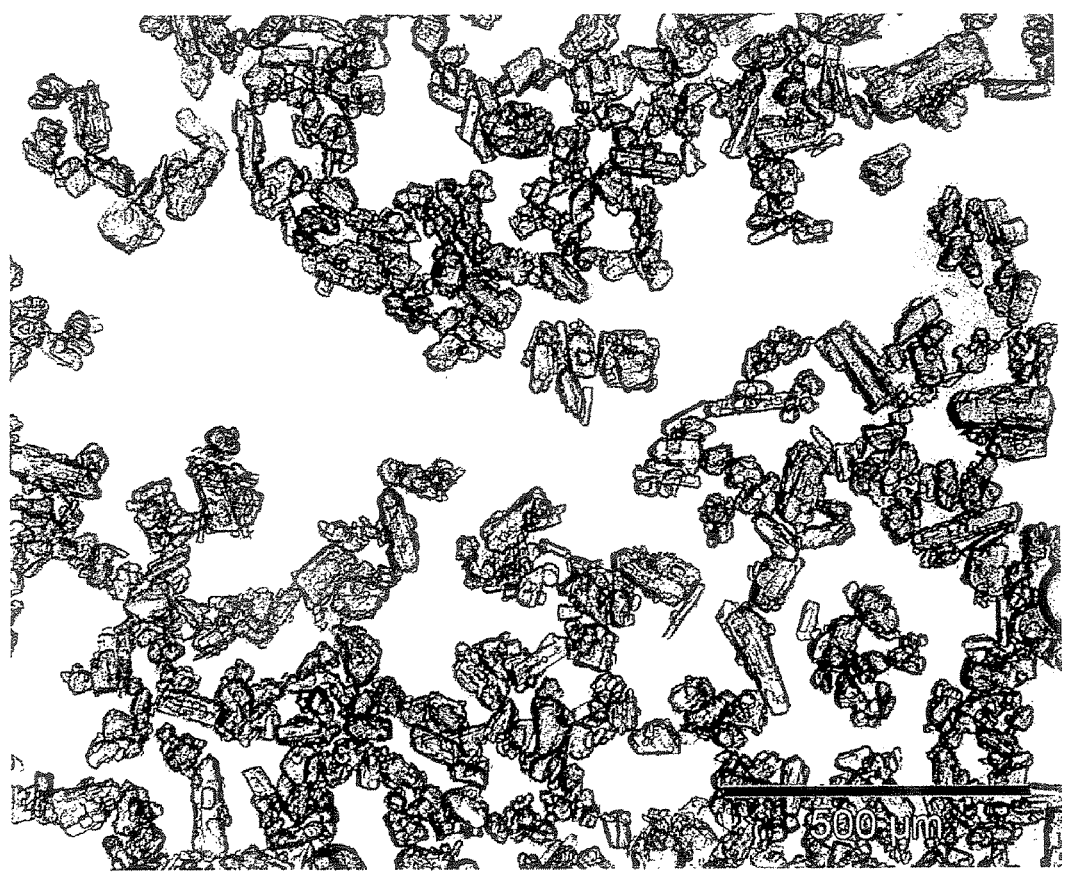
FIG. 2 is a microscopic view of MGDN crystals isolated by the inventive process of Example 2.

The 1 liter jacketed stirred vessel is initially charged with 1970 g of a 22% by weight aqueous MGDN emulsion at 70° C. The temperature-control fluid in the jacket is used to cool the solution to 57° C. This forms crystal seeds. Heating to 58° C. brings a portion of the solid formed back into solution. Subsequently, vacuum is applied and water is evaporated at an evaporation rate of 250 g/h at 58° C. and 170 mbar for two and a half hours. Afterward, the pressure in the crystallizer is reduced further to 40 mbar. The removed water vapor is then condensed and flows as condensate in its entirety back into the crystallizer. Within a further 2.5 hours, the suspension is cooled by brine cooling of the vessel wall at a rate of 20 K/h from 30° C. to an end temperature of 10° C. The cold suspension formed is filtered with a suction filter. The moist, beige filtercake is washed with 1.5 times the amount of water, after which it takes on a slightly yellowish color. The color number analysis of a 1% by weight solution of the resulting crystals in acetonitrile gives a Hazen color number of 48. As can be seen under the microscope (FIG. 2), a majority of the crystals consist of thick, needle-like crystals of length from 100 to 200 µm and thickness from 20 to 40 µm. No fines having a size of <1 µm can be seen.

Example 3

Figure 3:
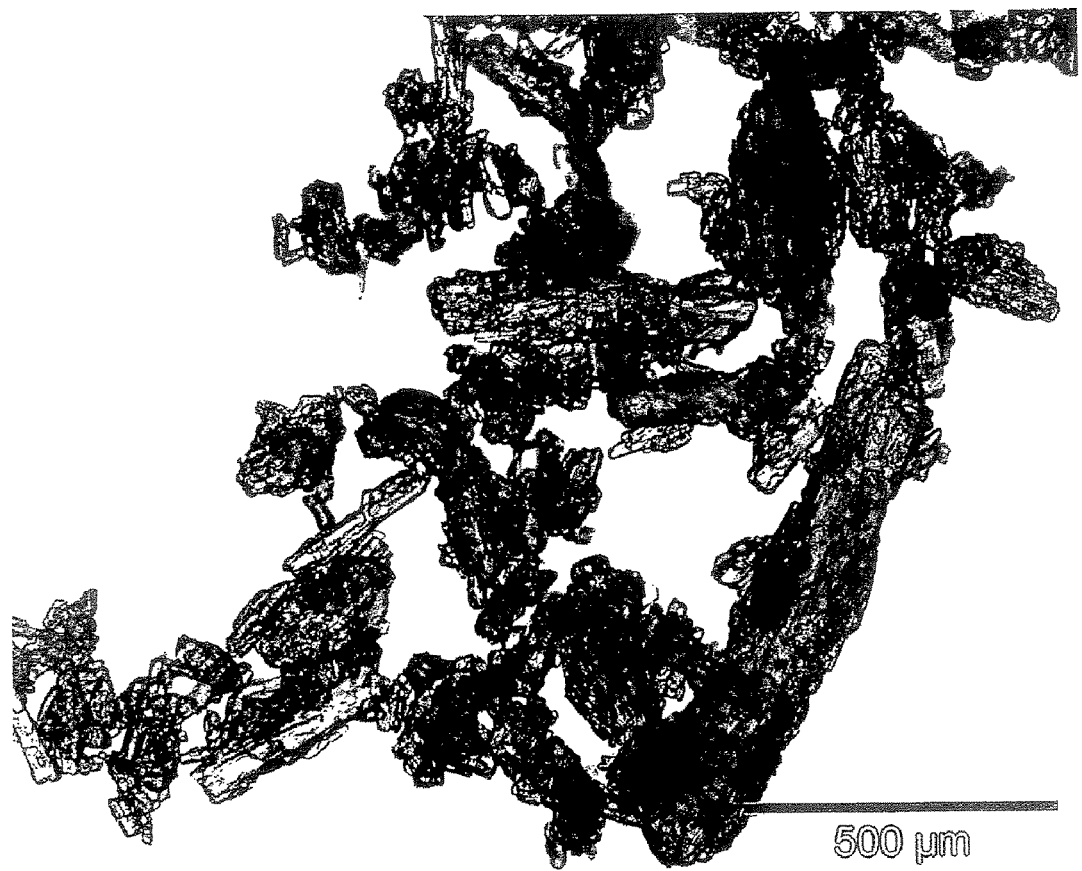
FIG. 3 is a microscopic view of MGDN crystals isolated by the inventive process of Example 3.

The crystallizer from example 1 is initially charged with 1300 g of a 30% by weight aqueous MGDN emulsion at 70° C. After the temperature has fallen below the solidification point and a hold phase of 40 min at 60° C., the solution is cooled to 10° C. at a rate of 12.5 K/h within 4 hours by evaporating at a pressure of from 170 to 40 mbar and with total reflux of the condensed water vapor. From approx. 30° C., the heat is removed by brine cooling by means of the jacket of the crystallizer. The suspension is charged into a sieve cup centrifuge and centrifuged at 2000 min$^{-1}$. Pale beige crystals are obtained. Under the microscope (FIG. 3), thick, needle-like crystals having a length of up to 1 mm and a thickness of up to 100 μm can be seen. No fines having a size of <1 μm can be seen. The color number analysis of 1% by weight solution of the crystals in acetonitrile gives a Hazen color number of 65.

What is claimed is:

1. A process for isolating methylglycinenitrile-N,N-diacetonitrile (MGDN) from an aqueous emulsion which comprises MGDN and has an MGDN content of 3-50% by weight in a crystallizer, comprising:
    (a) the aqueous emulsion is, starting from a temperature above the solidification point, cooled to a temperature below the solidification point, the cooling rate averaged over time not exceeding 5 K/h, until substantially the entirety of the emulsified MGDN has solidified, and
    (b) the resulting aqueous suspension is cooled further and/or concentrated, and the cooling rate may be greater than in step (a).

2. The process according to claim 1, wherein the aqueous emulsion is cooled in step (a) by allowing water to evaporate and/or by removing heat via the crystallizer wall.

3. The process according to claim 1, wherein the aqueous suspension is cooled and/or concentrated in step (b) by allowing water to evaporate.

4. The process according to claim 1, wherein heat is removed via the crystallizer wall in step (b) below a temperature of $\leq 30°$ C.

5. The process according to claim 1, wherein the cooling rate averaged over time in step (b) is at least 5 K/h.

6. The process according to claim 1, wherein cooling is effected in step (b) to a temperature below 20° C.

7. The process according to claim 1, wherein the aqueous emulsion comprising MGDN is obtained by reacting methylglycinenitrile with HCN and formaldehyde.

* * * * *